United States Patent
Archibald et al.

[11] 3,971,789
[45] *July 27, 1976

[54] O-(4-QUINOLYLAMINO)BENZAMIDES

[75] Inventors: John Leheup Archibald, Windsor; John Terence Arnott Boyle; John Christopher Saunders, both of Maidenhead, all of England

[73] Assignee: John Wyeth & Brother Limited, Taplow, England

[ * ] Notice: The portion of the term of this patent subsequent to Apr. 1, 1992, has been disclaimed.

[22] Filed: Jan. 23, 1975

[21] Appl. No.: 543,218

Related U.S. Application Data

[63] Continuation-in-part of Ser. No. 334,799, Feb. 22, 1973, Pat. No. 3,875,165.

[30] Foreign Application Priority Data

Oct. 21, 1972 United Kingdom............... 48593/72
Feb. 5, 1973 United Kingdom............... 5531/73

[52] U.S. Cl. .................. 260/286 R; 260/287 AR; 424/258
[51] Int. Cl.² ............. C07D 215/44; C07D 401/12
[58] Field of Search .................. 260/287 AR, 286 R

[56] References Cited
UNITED STATES PATENTS 3,875,165  2/1973  Archibald et al. ................ 260/287

*Primary Examiner*—Nicholas S. Rizzo
*Assistant Examiner*—David E. Wheeler

[57] ABSTRACT

The disclosure describes new 4-aminoquinoline derivatives of general formula

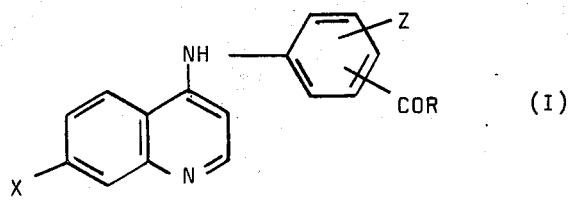

and their acid addition salts, where X is a halogen atom or a trifluoromethyl group, Z is a hydrogen atom or a defined substituent, R is group of the formula

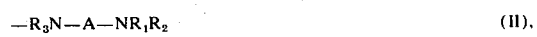

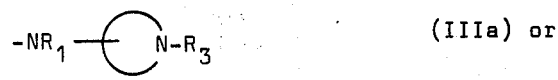

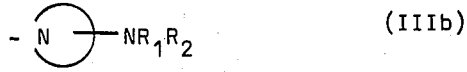

where A in formula II is a chain of 1 to 5 methylene groups which may be substituted with alkyl, the ring in formula IIIa and IIIb is a piperidine or pyrrolidine ring that may be substituted with alkyl and $R_1$, $R_2$ and $R_3$ represent hydrogen or certain defined substituents. The new 4-aminoquinoline derivatives show anti-malarial activity and, in some cases, show one or more of the following activities:- anti-inflammatory activity, anti-hypertensive activity, anti-trichomonal activity, inhibition of blood platelet aggregation, anti-ulcer activity and activity against allergic asthma. Compounds where —COR is in the o-position with respect to the 7-(halo or trifluoromethyl)-4-quinolylamino group and R is di(lower alkyl)aminopiperidino or —NR[10]R[11] where R[10] is hydrogen or lower alkyl and R[11] is di(-lower alkyl)amino(lower alkyl) or 1-(lower alkyl)-piperidyl show anti-inflammatory activity.

4 Claims, No Drawings

O-(4-QUINOLYLAMINO)BENZAMIDES

This application is a continuation-in-part of U.S. Ser. No. 334,799 entitled "4-Aminoquinoline Derivatives" filed Feb. 22, 1973 in the names of John Leheup Archibald, John Terence Arnott Boyle and John Christopher Saunders, now U.S. Pat. No. 3,875,165, granted Apr. 1, 1975 and entitled "(4-QUINOLYAMINO)-(N-PIPERIDYL)-BENZAMIDES AND N-[(4-QUINOLYLAMINO)BENZOYL]PIPERIDINES".

The invention provides new 4-aminoquinoline derivatives of the general formula

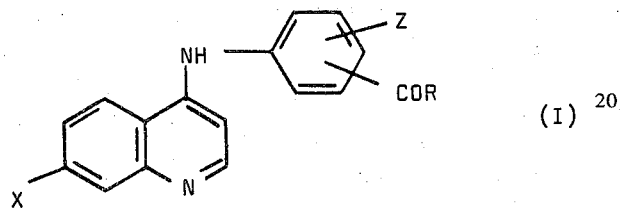

and their acid addition salts, where
  i. X is a halogen atom or a trifluoromethyl group;
  ii. Z is a hydrogen atom or a halogen atom, a trifluoromethyl group, a lower alkyl group, a lower alkoxy group, a hydroxyl group, a nitro group, an amino group or a mono- or di-alkyl substituted amino group, and
  iii. R represents a group of the formula

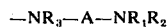
  —NR₃—A—NR₁R₂    (II)

or

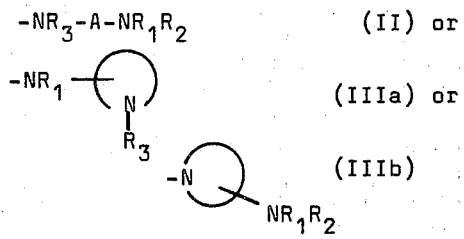

wherein
  a. in formula II A represents a chain of 1 to 5 methylene groups, which may be substituted by one or more alkyl groups;
  b. in formulas IIIa and IIIb the ring denotes a piperidine or pyrrolidine ring that may be substituted by one or more alkyl groups or by a divalent aliphatic chain substituting two different ring members of the piperidine or pyrrolidine ring;
  c. R₁ represents a hydrogen atom, an alkyl group, an aralkyl group, an acyl group or an aryl group or, in formula II or IIIb, R₁ and R₂ may together form the diacyl residue of a dicarboxylic acid or R₁ and R₂ may together form a divalent radical such that R₁R₂NH is a secondary cyclic amine with 5 to 7 ring atoms;
  d. R₂ is as defined above in connection with R₁ or represents a hydrogen atom, an alkyl group, an aralkyl group or an acyl group; and
  e. R₃ represents a hydrogen atom, an alkyl group, an aralkyl group, or an alkyl group substituted by a heterocyclic group, or an aliphatic chain joining the nitrogen atom member to another ring member of the ring in formula IIIa.

It will be apparent to those skilled in the art that the above definition of R includes moieties possessing an asymmetric carbon atom, especially for instance, in the cases where
  1. A is linear chain of 1 to 5 methylene groups, the chain being monosubstituted by methyl or ethyl, or
  2. R is of the formula IV or V

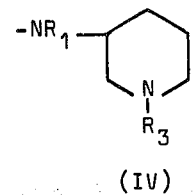   or   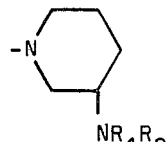

(IV)                               (V)

for example, in the cases where R denotes groups of the formula

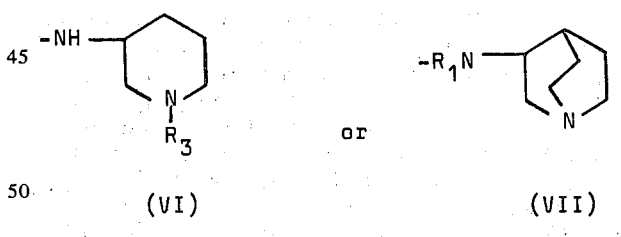

(VI)                               (VII)

where R₁, R₂ and R₃ may be, for instance, hydrogen or lower alkyl. It is to be understood that general formula I is intended to encompass both enantiomers where the compound contains an asymmetric carbon atom and mixtures of the enantiomers, for instance, racemic mixture of the enantiomers. General methods are recorded in the literature for the resolution of enantiomers.

In the compounds of the invention, X preferably represents a halogen atom, for example, a chlorine or bromine atom, but may also represent a trifluoromethyl group. Illustrative meanings of Z include hydrogen, chlorine, bromine atoms and trifluoromethyl, lower alkyl or alkoxy (for example, methyl, ethyl, propyl, butyl, methoxy, ethoxy, propoxy and butoxy), hydroxyl, nitro, amino, methylamino, ethylamino, dimethylamino and diethylamino groups.

In formula I the group denoted by —COR is preferably in the m- or p- position, advantageously the p-position, with respect for the 7-(halo or trifluoromethyl)-4-quinolylamino group. Certain compounds where the group denoted by —COR is in the o-position with respect to the 7-(halo or trifluoromethyl)-4-quinolylamino group are particularly interesting as anti-inflammatory agents as will be explained in more detail below.

In formula II and III$b$ R$_1$ and R$_2$ may be separate or may be joined together to form a divalent residue. The divalent residue is a diacyl residue of a dicarboxylic acid, for example, a group of the formula —CO—(CH$_2$)$_n$—CO where $n$ is 2 or 3 or

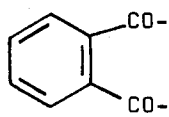

or is such that R$_1$R$_2$NH is a secondary cyclic amine with 5 to 7 ring atoms, for instance, piperidine, pyrrolidine or morpholine.

R$_1$, when in formula III$a$ or when separate from R$_2$ in formula II or III$b$, represents a hydrogen atom, an alkyl group, an aralkyl group, an acyl group or an aryl group. R$_2$, when separate from R$_1$ in formulae II and III$b$, represents a hydrogen atom, an alkyl group, an aralkyl group or an acyl group. R$_3$ in formulae II and III$a$ represents a hydrogen atom, an alkyl group, an aralkyl group, or an aliphatic chain joining the nitrogen ring atom to another ring atom of the ring shown in formula III$a$. Illustrative examples of such groups that can be denoted by R$_1$, R$_2$ or R$_3$ will now be described. Alkyl groups are desirably lower alkyl groups, for example, methyl, ethyl, n- or i- propyl and n-butyl. Aryl groups particularly comprehend phenyl or phenyl substituted by one or more substituents. As substituents for a phenyl group there may be employed lower alkyl (for example, methyl, ethyl, propyl or butyl), lower alkoxy (for example, methoxy, ethoxy, propoxy or butoxy), nitro, halogen, (preferably chlorine or bromine), hydroxy, trifluoromethyl or amino (including mono- or dialkylamino, for instance, dimethylamino). Aralkyl groups are aryl-substituted alkyl groups, where the alkyl group is desirably a lower alkyl group (e.g. methyl, ethyl, propyl or butyl) and its aryl substituent may be phenyl or substituted phenyl, in which the one or more substituents for phenyl are as mentioned above. Acyl groups particularly include the acyl groups of the formula —CO.R$_5$ where R$_5$ represents alkyl or aryl. As specific acyl groups there may be mentioned, for example, acetyl, propionyl, butanoyl, hexanoyl, benzoyl and benzoyl substituted by one or more of the above mentioned substituents for phenyl. As alkyl substituted by a heterocyclyl group there may be mentioned lower alkyl such as methyl, ethyl, propyl or butyl, substituted by thienyl (for instance 2-thienyl), furyl, pyrrolyl, imidazolyl, pyrazolyl (for instance 4-pyrazolyl), indolyl, pyridyl (for instance 2- or 4-pyridyl), quinolyl, thiazolyl (specifically 2-, 4- or 5-thiazolyl), isothiazolyl or oxazolyl.

As examples of A in formula II there may be mentioned methylene, dimethylene, trimethylene, tetramethylene, and pentamethylene and their mono- or di-(lower alkyl) substitution products, for example, groups of the formulae

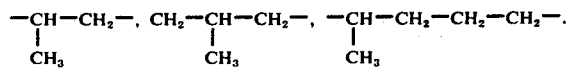

The piperidine or pyrrolidine ring shown in formulae III$a$ and III$b$ may be substituted with one or more alkyl groups, preferably lower alkyl groups, for example, methyl, ethyl, propyl or butyl. As examples of R containing a piperidine or pyrrolidine ring there may be mentioned groups of the formula:

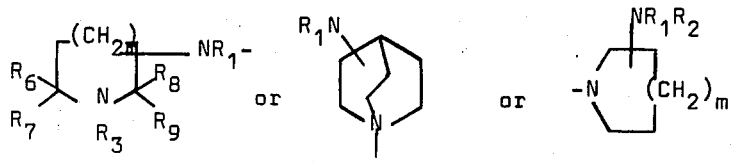

(VIII)    (VII)    (IX)

where $m$ is 0 or 1; R$_1$, R$_2$ and R$_3$ are as defined above; and R$_6$, R$_7$, R$_8$ and R9, which may be the same or different may be hydrogen or lower alkyl, for instance, methyl, ethyl, propyl or butyl.

The term "lower" as used herein in connection with such groups as "alkyl" or "alkoxy" denotes that the group contains up to 6 carbon atoms, preferably up to 4 carbon atoms.

Examples of acid addition salts are those formed from inorganic and organic acids and in particular pharmaceutically acceptable acid addition salts such as the sulphate, hydrochloride, hydrobromide, hydroiodide, nitrate, phosphate, sulphonate (such as the methanesulphonate and p-toluenesulphonate), acetate, maleate, fumarate, tartrate, malonate, citrate and formate.

The compounds of the invention may be made by building the compound up by known reactions. In particular the amide linkage shown in formula I as -COR may be formed by acylation of an appropriate amine, and an amino- substituted benzamide may be converted to the secondary amine by introducing the 7-(halo or trifluoromethyl)-4-quinolyl group in known manner.

The invention provides a method of making compounds of the formula I and their acid addition salts wherein a. a compound of the formula RH, where R is as defined in connection with formula I, or, where necessary or desired, a corresponding compound with a protecting group, or a corresponding compound with an activated amino group, is acylated with a compound of formula (XIII)

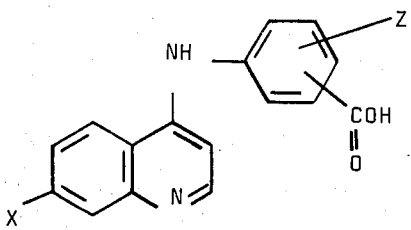

(wherein X and Z are as defined above in connection with formula I), or a corresponding compound with a protecting group, or a reactive derivative of the compound of formula (XIII) or its corresponding compound with a protecting group; or b. a compound of the formula XIV

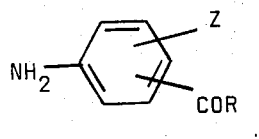

(where R and Z are as defined in connection with formula I) or a corresponding compound with a protecting group, is reacted with a compound of formula (XV)

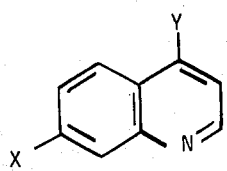

(where X is as defined above in connection with formula I and Y denotes a group or atom replaceable by nucleophilic attack by compound of formula XIV), Y is for example, an iodine atom, a bromine atom or a chlorine atom or an organosulphonyloxy group, for instance, p-toluenesulphonyloxy. Where necessary or if desired, the process may also include removal of a protecting group and, if desired, conversion of a free base form of compound of formula I into an acid addition salt form or conversion of an acid addition salt form of a compound of formula I into the corresponding free base form.

Starting materials of formula RH and formulae XIV and XV are known compounds or, if new, are accessible by conventional methods.

The acylation method may be carried out by reacting the compound of formula XIII with the compound of formula RH or a corresponding compound with a protecting group, in the presence of a condensing agent, for instance, a carboxiimide. Alternatively, the acid of formula XIII may be reacted with a compound in which an amino function has been activated, for example, by forming the phosphazo derivative. The reactive acylating derivatives of the compound of formula XIII may be employed, for example, active esters, acyl halides, simple or mixed anhydrides and the acid azide. The acid halides, particularly the acid chloride are especially suitable. The acylation product may be recovered from the reaction mixture by standard isolation procedures.

It will be apparent to those skilled in the art that certain unacylated compounds of formula RH may present more than one potentially reactive location for acylation. Undesired acylation may be avoided by chemical protection with removable blocking groups or other means. For example, the compounds of the formula

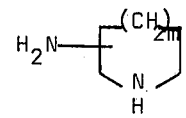

(where $m$ is 0 or 1) may be acylated at the $NH_2$ function by forming a derivative with an activated amino group, for example, the phosphazo derivative, and reacting said derivative with the acid of formula XIII. Alternatively, the compounds of formula XVI may be acylated at the ring nitrogen atom by using a starting material in which the $NH_2$ function is protected with a blocking group which is removed after acylation. Compounds of formula I and their acid addition salts, in which, in formula IIIa, $R_3$ denotes hydrogen, may be prepared by using, for example, a benzyl group as removable protecting group. Thus a starting compound of formula

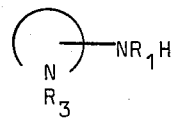

in which $R_3$ is benzyl is acylated and the protecting group is removed after acylating by debenzylation. Debenzylation may be carried out using sodium in liquid ammonia or by catalytic hydrogenation under conditions such that the 7-halo- or 7-trifluoromethyl substituent on the quinolyl group is not removed. In addition, compounds of formula RH include compounds where a substituent on an aryl group or heterocyclyl group is susceptible to acylation, e.g. a free hydroxyl or amino substituent. Such substituents may be protected with a removable blocking group which is cleaved off after acylation. Acylating derivatives of the acid of formula XIII may include protection for a group Z sensititve to acylation. For example, a final product in which Z is an amino function can be formed by using an acylating derivative of the acid of formula

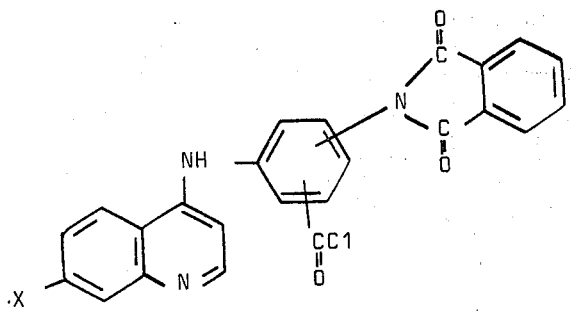

(XVII)

and converting the phthalimido group to an —NH₂ group by reaction with hydrazine. The new compounds of the invention are normally quite stable to hydrolysis under acid conditions and therefore favour protecting groups that are readily hydrolysed off under acid conditions.

Compounds of the formula XIV are accessible in standard manner, for example, by acylation of a compound of formula RH where R has the meanings given in connection with formula I with an acylating derivative of a nitrobenzoic acid or (protected amino) benzoic acid and subsequent reduction of the nitro group or removal of the amino protecting group. The reaction of the primary amine XIV with the compound of formula XV may be carried out in conventional manner for amination of 4-substituted quinolines. The reaction products may be recovered from the reaction mixtures by standard isolation procedures. In certain cases it is expedient to incorporate a protecting group for amino in the compound of formula XIV to reduce or preclude undesired reaction of the compounds of formula XV with a primary or secondary amino function in the group R. In such cases the protecting group is removed after the reaction with the compound of formula XV.

The compounds of the present invention may be isolated in free base form or as acid addition salts. Acid addition salts may be converted into the free bases in conventional manner. The free base forms may be converted into acid addition salts in conventional manner, for instance, by adding ethereal hydrogen chloride to a solution of the free base where a hydrochloride salt is desired.

The compounds of the present invention are indicated for pharmacological usage and, in some cases, for use as intermediates for the preparation of other compounds of formula I. For instance, the compounds of the invention generally demonstrate anti-malarial activity and, in some cases, also demonstrate at least one of the following activities: anti-inflammatory activity, anti-hypertensive activity, anti-trichomonal activity, inhibition of blood platelet aggregation, anti-ulcer activity and activity against allergic asthma. The anti-malarial activity is particularly interesting, especially since the anti-malarial compounds of the invention generally possess the advantage of being less toxic than chloroquine, a known anti-malarial compound, in such test animals as mice. The inhibition of blood platelet aggregation demonstrated by 3-(p-[7-chloro-4-quinolylamino]benzamido)-1-ethylpiperidine is also particularly interesting. Some of the compounds of the invention may also be used as intermediates for the preparation of other compounds conforming with formula I. For example, compounds containing a phthalimido group as —NR₁R₂ in formula II or IIIb may be subjected to cleavage using hydrazine to form a corresponding compound containing an amino group (—NH₂) as —NR₁R₂ and compounds containing an amino group may be alkylated to form a corresponding compound with an alkyl-substituted amino group.

The compounds can be tested for anti-malarial activity by the following procedure:

Five mice are infected with a lethal dose of *Plasmodium Berghei* three days prior to administration of the compound at various dose levels. The compound test does is in milligrams per kilogram of body weight. Routinely, the compounds are administered subcutaneously in oil.

Extension of the survival time beyond the mean survival time of infected control mice is interpreted as evidence of anti-malarial activity. A 60 day survival time is regarded as evidence of a cure.

The invention also includes pharmaceutical compositions containing as active ingredients a compound of formula (I) or a pharmaceutically acceptable acid addition salt thereof, which may be micronised if desired. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportion and compacted in the shape and size desired. The powders and tablets preferably contain from 5 to 99, preferably 10–80% of the active ingredient. Suitable solid carrier are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; it it is too insoluble for this it can often be dissolved in a suitable organic solvent, for instance aqueous propylene glycol or polyethylene glycol solutions. Aqueous propylene glycol containing from 10 to 75 percent of the glycol by weight is generally suitable. In other instances compositions can be made by dispersing the finely divided active ingredient in aqueous starch or sodium carboxymethyl cellulose solution, or in a suitable oil, for instance arachis oil. Liquid pharmaceutical compositions which are sterile or suspensions can be utilised by intramuscular, intraperitoneal or subcutaneous injection. In many instance a compound is orally active and can be administered orally either in liquid or solid composition form.

Preferably the pharmaceutical composition is in unit dosage form. In such form, the composition is subdivided in unit dosages containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The present invention particularly provides new 4-aminoquinoline derivatives of the general formula I as illustrated above and their pharmaceutically acceptable acid addition salts, wherein X and Z are as defined above and the group —COR is in the o-position with respect to the 7-(halo or trifluoromethyl)-4-quinolylamino group and R is selected from di(lower alkyl)aminopiperidino and a group of the formula:

where $R^{10}$ is selected from hydrogen and lower alkyl and $R^{11}$ is selected from di(lower alkyl)amino(lower alkyl) and 1-(lower alkyl)piperidyl. The term "lower alkyl" means an alkyl group containing up to 6 carbon atoms, preferably up to 4 carbon atoms. As illustrative meanings of $R^{10}$, there may be mentioned, hydrogen, methyl, ethyl, propyl, butyl and hexyl. As illustrative meanings of di(lower alkyl)amino(lower alkyl), there may be mentioned di(methyl)aminomethyl, di(ethyl)aminoethyl, N-methyl-N-ethylaminopropyl, di(ethyl)aminobutyl and di(butyl)aminoethyl. As illustrative meanings of 1-(lower alkyl)piperidyl there may be mentioned 1-ethyl-2-piperidyl, 1-ethyl-3-piperidyl, 1-ethyl-4-piperidyl, 1-methyl-3-piperidyl, 1-propyl-3-piperidyl, 1-butyl-4-piperidyl and 1-pentyl-3-piperidyl. As illustrative meanings of di(lower alkyl)aminopiperidino there may be mentioned 4-dimethylaminopiperidino and 3-dibutylaminopiperidino.

The new 4-aminoquinoline derivatives having the formula:

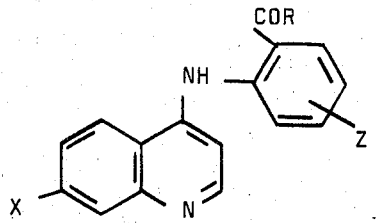

wherein X, Z and R are as defined in the preceding paragraph and their pharmaceutically acceptable acid addition salts are pharmacologically useful. In particular they show activity as anti-inflammatory agents and, in some cases particularly 2-(7-choro-4-quinolylamino)-N-(2-diethylaminoethyl)-N-ethylbenzamide and 2-(7-chloro-4-quinolylamino)-N-(1-ethyl-3-piperidyl)benzamide, show anti-hypertensive activity. 2-(7-Chloro-4-quinolylamino)-N-(2-diethylaminoethyl)-N-ethylbenzamide also inhibits blood platelet aggregation. The compounds are tested for activity by standard testing procedures. A literature reference for a procedure for testing for anti-inflammatory activity is Newbould, B. B. Brit. Jour. Pharm. Chemoth., 21, 127–136)1963).

The following examples illustrate the invention:

EXAMPLE 1

2-(7-Chloro-4-quinolylamino)-N-(1-ethyl-3-piperidyl)-benzamide

A solution of 10.05 grams of 2-(7-chloro-4-quinolylamino)benzoic acid hydrochloride in 60 milliliters of thionyl chloride was refluxed for two hours. After evaporation of the thionyl chloride 50 milliliters of benzene was added and the mixture re-evaporated to give the acid chloride as a pinkish solid. This was then added in portions to a stirred, ice-cooled solution of 3.84 grams of 3-amino-1-ethyl piperidine in 60 milliliters of chloroform with 80 milliliters of water and 31.8 grams of sodium carbonate. After the addition was complete the mixture was stirred at room temperature overnight, filtered and the filtrate (chloroform-water) separated, the aqueous layer further extracted with chloroform, the chloroform extracts combined, dried over magnesium sulphate and evaporated to give a brown gum. Trituration with n-hexane gave 8.9 grams of the title compound as the hemihydrate. Melting point: 187°–188°C.

ANALYSIS: Found: C, 66.5%; H, 6.23%; N, 13.4%. $C_{23}H_{25}ClN_4O·½H_2O$ requires C, 66.1%; H, 6.27%; N, 13.4%.

EXAMPLE 2

2-(7-Chloro-4-quinolylamino)-N-(2-diethylaminoethyl)-N-ethylbenzamide

A solution of 10.05 grams of 2-(7-chloro-4-quinolylamino)benzoic acid hydrochloride in 60 milliliters of thionyl chloride was refluxed for two hours. After evaporation of the thionyl chloride 50 milliliters of benzene was added and the mixture re-evaporated to give the acid chloride as a yellowish solid. This was then added in portions to a stirred, ice-cooled solution of 4.33 grams of N,N,N¹triethylethylene-diamine in 60 milliliters of chloroform with 100 milliliters of water and 31.8 grams of sodium carbonate. After the addition was complete the mixture was stirred at room temperature overnight, filtered and the filtrate (chloroform-water) separated, the aqueous layer further extracted with chloroform, the chloroform extracts combined, dried over magnesium sulphate and evaporated to give 16 grams of a brown gum. This was dissolved in 250 milliliters of ether and ethereal hydrogen chloride added to precipitate 14.4 grams of the title compound as the hydrochloride dihydrate. Melting point: 155°C.

ANALYSIS: Found: C, 54.0%; H, 6.30%; N, 10.2%. $C_{24}H_{29}ClN_4O \cdot 2HCl \cdot 2H_2O$ requires C, 54.0%; H, 6.61%; N, 10.5%.

EXAMPLE 3

2-(7-Chloro-4-quinolylamino)-N-(2-diethylaminoethyl)benzamide

A solution of 6.7 grams of 2-(7-chloro-4-quinolylamino)benzoic acid hydrochloride in 40 milliliters of thionyl chloride was refluxed for two hours. After evaporation of the thionyl chloride 50 milliliters of benzene was added and the mixture re-evaporated to give the acid chloride as a pinkish solid. This was then added in portions to a stirred ice-cooled solution of 2.32 grams of N,N-diethylethylenediamine in 40 milliliters of chloroform with 100 milliliters of water and 21.2 grams of sodium carbonate. After the addition was complete the mixture was stirred at room temperature overnight, filtered and the filtrate (chloroform-water) separated, the aqueous layer further extracted with chloroform, the chloroform extracts combined, dried over magnesium sulphate and evaporated to give an oil. This was dissolved in 200 milliliters of ether and ethereal hydrogen chloride added to precipitate 7.4 grams of the title compound as the dihydrochloride hydrate. Melting point: 225°C.

ANALYSIS: Found: C, 51.2%; H, 5.99%; N, 10.6%. $C_{22}H_{25}ClN_4O \cdot 2HCl \cdot 2\frac{1}{2}H_2O$ requires C, 51.3%; H, 6.26%; N, 10.9%.

EXAMPLE 4

N-(1-n-Butyl-4-piperidyl)-2-(7-chloro-4-quinolylamino)-3-methyl benzamide a. 4,7-Dichloroquinoline and 2-amino-3-methyl benzoic acid are refluxed in dilute hydrochloric acid for 1 hour to give 2-(7-chloro-4-quinolylamino)-3-methyl benzoic acid.

b. 2-(7-Chloro-4-quinolylamino)-3-methyl benzoic acid is converted to the acid chloride which is reacted with 4-amino-1-n-butyl piperidine as in Example 1 to give the title compound.

EXAMPLE 5

4-Chloro-2-(7-chloro-4-quinolylamino)-N-(2-di-n-butylaminoethyl)benzamide a. 4,7-Dichloroquinoline and 2-amino-4-chloro benzoic acid are refluxed in dilute hydrochloric acid for 1 hour to give 4-chloro-2-(7-chloro-4-quinolylamino)-benzoic acid.

b. 4-Chloro-2-(7-chloro-4-quinolylamino)benzoic acid is converted to the acid chloride which is reacted with 2-(di-n-butylamino)ethylamine as in Example 1 to give the title compound.

EXAMPLE 6

1-[2-(7-Chloro-4-quinolylamino)-5-iodo-benzoyl]-4-dimethylamino piperidine a. 4,7-Dichloroquinoline and 2-amino-5-iodo benzoic acid are refluxed in dilute hydrochloric acid for 1 hour to give 2-(7-chloro-4-quinolylamino)-5-iodo benzoic acid.

b. 2-(7-Chloro-4-quinolylamino)-5-iodo benzoic acid is converted to the acid chloride which is reacted with 4-dimethylamino piperidine as in Example 1 to give the title compound.

EXAMPLE 7

N-(3-Dimethylaminopropyl)-2-(7-trifluoromethyl-4-quinolylamino)benzamide a. 4-Chloro-7-trifluoromethylquinoline and 2-amino benzoic acid are refluxed in dilute hydrochloric acid for 1 hour to give 2-(7-trifluoromethyl-4-quinolylamino)benzoic acid.

b. 2-(7-Trifluoromethyl-4-quinolylamino)benzoic acid is converted to the acid chloride which is reached with 3-dimethylaminopropylamine as in Example 1 to give the title compound.

EXAMPLE 8

1-[2-(7-Bromo-4-quinolylamino)-benzoyl]-4-diethylamino piperidine a. 7-Bromo-4-chloro-quinoline and 2-amino benzoic acid are refluxed in dilute hydrochloric acid for 1 hour to give 2-(7-bromo-4-quinolylamino) benzoic acid.

b. 2-(7-Bromo-4-quinolylamino)benzoic acid is converted to the acid chloride which is reacted with 4-diethylamino piperidine as in Example 1 to give the title compound.

We claim:

1. A compound selected from those having the formula

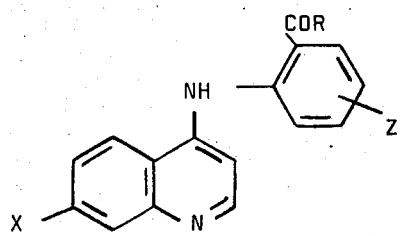

and their pharmaceutically acceptable acid addition salts, wherein X is selected from halogen and trifluoromethyl; Z is selected from the group consisting of hydrogen, halogen and lower alkyl; and R is selected from di(lower alkyl)aminopiperidino and a group having the formula

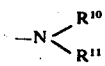

wherein $R^{10}$ is selected from hydrogen and lower alkyl and $R^{11}$ is selected from di(lower alkyl)amino(lower alkyl) and 1-(lower alkyl)piperidinyl.

2. A compound as defined in claim 1 which is selected from 2-(7-chloro-4-quinolylamino)-N-(1-ethyl-3-piperidyl)benzamide and the pharmaceutically acceptable acid addition salts thereof.

3. A compound as defined in claim 1 which is selected from 2-(7-chloro-4-quinolylamino)-N-(2-diethylaminoethyl)-N-ethylbenzamide and the pharmaceutically acceptable acid addition salts thereof.

4. A compound as defined in claim 1 which is selected from 2-(7-chloro-4-quinolylamino)-N-(2-diethylaminoethyl)benzamide and the pharmaceutically acceptable acid addition salts thereof.

* * * * *